(12) United States Patent
Baiker et al.

(10) Patent No.: US 6,646,135 B1
(45) Date of Patent: Nov. 11, 2003

(54) CONTINUOUS PROCESS FOR THE ENANTIOSELECTIVE HYDROGENATION OF ALPHA KETOCARBONYL COMPOUNDS

(75) Inventors: Alfons Baiker, Opfikon (CH); Niklaus Künzle, Wil (CH); Tamas Mallat, Zürich (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/568,353

(22) Filed: May 10, 2000

(30) Foreign Application Priority Data

Jun. 23, 1999 (EP) ................................ 99112078

(51) Int. Cl.$^7$ .................. C07D 305/12; C07C 69/66; C07C 29/14
(52) U.S. Cl. .................. 549/319; 560/179; 568/880
(58) Field of Search .................. 560/179; 568/880; 549/319

(56) References Cited

U.S. PATENT DOCUMENTS 4,329,487 A    5/1982   Orito et al.

FOREIGN PATENT DOCUMENTS

GB    WO-9738955 A1 * 10/1997

OTHER PUBLICATIONS

Minder et al, Enantioselective Hydrogenation of Ethyl Pyruvate in Supercritical Fluids, 1995, Catalysis Letters, 34(12), pp. 1–9. Complete Document.*

Minder et al Catalysis Letters 1995, 34(12). pp. 1–9, Abstract Only.*

Schürch, et al., "Enantioselective Hydrogenation of Ketopantolactone: Effect of Stereospecific Product Crystallization During Reaction," *Journal of Catalysis*, vol. 176, pp. 569–571 (1998).

Schürch, et al., "Enantioselective Hydrogenation of Ketopantolactone," *Journal of Catalysis*, vol. 169, pp. 275–286 (1997).

Derwent English language abstract of JP 62158268 (1987).

Patent Abstracts of Japan, vol. 011, No. 398, of JP 62158268 (1987).

Patent Abstracts of Japan, vol. 004, No. 069, of JP 55035060 (1980).

* cited by examiner

*Primary Examiner*—Johann Richter
*Assistant Examiner*—Paul A. Zucker
(74) *Attorney, Agent, or Firm*—Bryan Cave LLP

(57) ABSTRACT

The invention relates to a continuous process for enantioselective catalytic hydrogenation of an alpha ketocarbonyl compound such as alpha ketoesters and alpha ketolactones to produce an alpha hydroxy carbonyl compound.

14 Claims, 2 Drawing Sheets

CONTINUOUS PROCESS FOR THE ENANTIOSELECTIVE HYDROGENATION OF ALPHA KETOCARBONYL COMPOUNDS

FIELD OF THE INVENTION

The present invention relates to a continuous process for the enantioselective hydrogenation of alpha ketocarbonyl compounds. In particular, the invention relates to a continuous process for the enantioselective hydrogenation of alpha-ketoesters and alpha-ketolactones.

BACKGROUND OF THE INVENTION

Orito, et al., U.S. Pat. No. 4,329,487 ("Orito '487") describes a method for the asymmetric hydrogenation of alpha-ketoesters which includes subjecting an alpha-ketoester to asymmetric hydrogenation in the presence of a platinum-alumina catalyst modified with a solution of a cinchona-alkaloid selected from at least one member of the group of quinine, quinidine, cinchonidine and cinchonine.

According to Orito '487, alpha-ketoesters are reacted by a batch reaction accomplished in a pressure container such as an autoclave.

The hydrogenation of ketopantolactone over a cinchonidine modified Pt-alumina catalyst in a batch process has been investigated and described by A. Baiker et al. in Journal of Catalysis, 176, 569–571, (1998).

Japanese patent publication JP 62158268 describes the asymmetric hydrogenation of alpha ketolactones in a batch process in the presence of a platinum-carbon catalyst modified with a solution of a cinchona-alkaloid selected from at least one of quinine, cinchonine or cinchonidine. The preparation of the catalyst includes mixing 0.5 g 5% Pt/C with 40 ml 1% cinchonidine/ethanol and refluxing the mixture for 3 hours. The catalyst is separated with a centrifuge. A mixture of the catalyst and e.g. ketopantolactone in benzene is autoclaved to give D-pantolactone. The reaction temperature is about 10 to about 100° C. (e.g., room temperature). The hydrogen pressure is normal pressure to about 100 kg/cm$^2$, preferably about 60 kg/cm$^2$.

The drawback of the batch process is the huge reactor volume needed for reaction and solid-liquid separation. Another drawback of the batch process is the need for a stirrer which leads to mechanical abrasion of catalyst particles (M. Garland, H. P. Jalett and H. U. Blaser, *Stud. Surf. Sci. Catal.* 59 (1991) 177).

SUMMARY OF THE INVENTION

It is an object of the present invention to provide a process that overcomes the aforesaid drawbacks, and still preserves the high enantioselectivity characteristic of the batch process.

It has now been found that it is possible to carry out the hydrogenation of alpha-ketocarbonyl compounds continuously.

Thus, the present invention includes a continuous process for catalytic hydrogenation of a substrate containing or consisting of an alpha ketocarbonyl compound which process includes the steps of:

(i) contacting in a reactor a substrate and hydrogen in the presence of a modified platinum catalyst, optionally in the presence of a solvent and, for example, a supercritical co-solvent, at a temperature of from about −20° C. to about 100° C. and at pressures ranging from about 2 bar to about 150 bar to convert the alpha ketocarbonyl compound to the corresponding alpha hydroxy carbonyl compound;

(ii) continuously feeding the substrate which optionally contains a modifier to the reactor;

(iii) continuously feeding hydrogen to the reactor;

(iv) continuously discharging the reaction product from the reactor; and (v) recovering the alpha hydroxy carbonyl compound from the reaction product.

Another embodiment of the invention is a process for making alpha hydroxy carbonyl from alpha ketocarbonyl which includes:

(i) continuously feeding a substrate solution and a modified platinum catalyst into an apparatus wherein the substrate solution includes an alpha ketocarbonyl/ compound;

(ii) continuously feeding hydrogen into the apparatus;

(iii) continuously discharging a reaction product from the reactor, wherein the temperature in the apparatus is from about −20° C. to about 100° C. and the pressure in the apparatus is about 2 to about 150 bar.

DETAILED DESCRIPTION OF THE INVENTION

Figure 1:
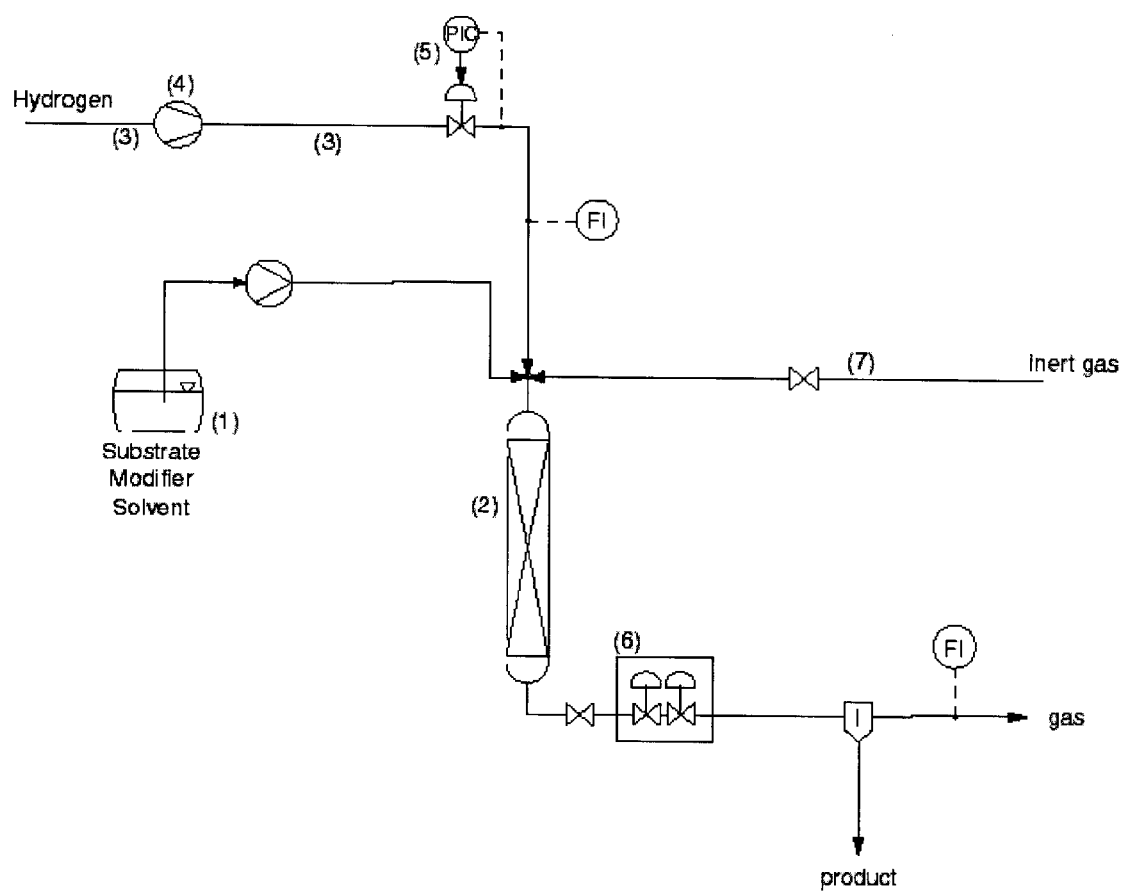
FIG. 1 shows a flow diagram (in schematic form) of a hydrogenation apparatus according to one embodiment of the invention. A solid alpha ketocarbonyl compound is dissolved in an organic solvent, thus forming the substrate. The modifier is added to the substrate. Examples 1 and 2 of the invention refer to a hydrogenation process carried out according to FIG. 1.

As used herein the term "substrate" means a solution of a solid alpha ketocarbonyl compound or a liquid alpha ketocarbonyl compound. If appropriate, the liquid alpha ketocarbonyl compound can be mixed with a solvent.

In the present invention, the term "alpha ketocarbonyl compound" refers to alpha ketolactones such as alpha ketopantolactone or to alpha-ketoesters such as, for example, esters of alpha ($C_1$–$C_6$) alkyl ketopropionic acid or esters of alpha aryl ketopropionic acid. An example of an alpha ($C_1$–$C_6$) alkyl ketopropionic acid ester is pyruvic acid ethyl ester ($CH_3COOOC_2H_5$). An example of an alpha aryl ketopropionic acid ester is benzoylformic acid ethyl ester (Phenyl-$COCOOC_2H_5$).

A preferred solid alpha ketocarbonyl compound is alpha ketopantolactone. A preferred liquid alpha ketocarbonyl compound is pyruvic acid ethyl ester.

Suitable solvents to dissolve a solid alpha ketocarbonyl compound according to the present invention include organic solvents and mixtures of organic solvents with water. Suitable solvents to be mixed with a liquid alpha ketocarbonyl compound include organic solvents, supercritical solvents and mixtures of organic solvents with water.

Suitable organic solvents include aromatic solvents such as, for example, toluene, benzene, cumene; aliphatic solvents such as hexane, cyclohexane, pentane, cyclopentane, diethylether, tetrahydrofuran, acetic acid, alcohols, acetone, formamides and mixtures thereof. A preferred alcohol is, e.g., ethanol or propanol. A preferred formamide is, e.g., dimethylformamide.

Addition of small amounts (0.1–5 wt %) of carboxylic acids (e.g., acetic acid, trifluoracetic acid) or amines (e.g., triethyl amine, quinoline) can also be useful in the present invention.

In the present invention, the choice of the solvent is not critical. Any solvent capable of dissolving the alpha ketocarbonyl compound can be used in this invention. If a solvent is present the reaction is preferably carried out in a supercritical state.

Suitable solvents or co-solvents for carrying out the reaction in a supercritical state are selected from the group of methane, ethane, propane, carbon dioxide, sulfurhexafluoride, chlorinated- and fluorinated solvents and the like.

As used herein, the term "platinum catalyst" refers to platinum metal deposited onto a variety of supports such as carbon black, calcium carbonate, activated alumina, silica or zeolithes. These catalysts are well known and commercially available. Suitable catalysts contain about 0.5 wt % to about 10 wt % of platinum. For example, a catalyst containing 5 wt % of platinum deposited onto alumina is sold by Engelhard Corp. with the code number 4759. The catalyst is charged into a fixed bed reactor. A metal loading of more than 5 wt % of platinum may require dilution of the catalyst bed with inert beads.

As used herein, the term "modified platinum catalyst" refers to a platinum catalyst modified by contacting the platinum catalyst with a solution of a cinchona-alkaloid or derivatives thereof, 2-hydroxy-2-aryl-ethylamine or derivatives thereof, 1-aryl-ethylamine or derivatives thereof.

Suitable cinchona alkaloids for use in the present invention include, for example, quinine, hydroquinine, cinchonidine, 10-11-dihydrocinchonidine, O-methyl-cinchonidine, 10-11-dihydro-O-methyl-cinchonidine epiquinidine, epicinchonidine, cinchonine, epicinchonine, epiquinine, hydroquinidine, 4-chlorobenzoate-epiquinine or 4-chlorobenzoate-epicinchonine. Preferred cinchona alkaloids are cinchonidine and dihydrocinchonidine.

Examples of 2-hydroxy-2-aryl-ethylamines or derivatives thereof include 2-(1-pyrrolidinyl)-1-(1-naphthyl)ethanol, 2-(1-pyrrolidinyl)-1-(4-azanaphthyl)ethanol and 2-(1-(N,N-dimethyl) amino)-1-(1-naphtyl)ethanol.

Examples of 1-aryl-ethylamines or derivatives thereof include 1-(1-naphtyl)-ethlyamine, 1-(1-naphtyl)-(N-methyl)-ethylamine, 1-(1-naphtyl)-(N-propyl)-ethylamine and N-[1'-(1-naphtyl)ethyl]-2-amino propionic acid ethyl ester.

In the present invention, the modifiers are amine bases. The modifiers may be used as free bases or as a salt with an acid, such as, for example, HCl, $HClO_4$, $CF_3COOH$. A commercially available modifier useful in the present invention is cinchonidine hydrochloride.

The modifier can be added to the substrate before starting the hydrogenation process, thus modifying the platinum catalyst when flowing through the reactor vessel or the platinum catalyst can be modified by immersing the platinum catalyst into a solution of the modifier before charging the reactor vessel with the catalyst. It is preferred to add the modifier to the substrate before starting the hydrogenation process.

The modifier is generally added in the form of a solution. Any organic solvent capable of dissolving the modifier may be used, such as the organic solvents set forth above. Preferably the same solvent is used to dissolve the modifier and the alpha ketocarbonyl compound.

There is no limit to the reactor size as long as a sufficient heat transfer is guaranteed. A suitable reactor vessel consists of a 1 to 40 ml stainless steel or inconel tube heated with electrical heating tape or cooled with a cooling jacket. A thermocouple measures the temperature in the center of the tube. The catalyst bed consists, for example, of about 0.1 to about 20 g of catalyst depending on the volume of the reactor. However, reactors of other types and size that are appropriate for conducting a continuous hydrogenation can be used.

At the end of the process the reaction product is discharged from the reactor vessel and the alpha hydroxy carbonyl compound is recovered by methods well known in the art such as crystallization or distillation.

The following examples are provided to further illustrate the process of the present invention. These examples are illustrative only and are not intended to limit the scope of the invention in any way.

EXAMPLES

Examples 1–4

The process of the present invention as set forth in FIG. 1 is typically initiated by dissolving the alpha ketocarbonyl compound and the modifier in vessel (1). The resulting solution contains from about 0.1 wt % to about 100 wt % of the alpha ketocarbonyl compound and from about $1 \times 10^{-5}$ wt % to about 0.5 wt % of modifier.

The mass flow is started at the reaction temperature, for example, at 17° C. or 20° C. (Examples 1 and 2, respectively). The above solution containing an alpha ketocarbonyl compound and a modifier is pumped into the fixed bed reactor (2) and contacted with hydrogen to start the hydrogenation reaction. Before catalytic runs, the reactor is flushed with nitrogen.

Subsequently, the content of vessel (1) is continuously pumped into the fixed bed reactor. The solution flow rate is preferably from about 0.1 to about 50 ml/minute, the preferred flow of the alpha ketocarbonyl compound is $2 \times 10^{-5} - 2 \times 10^{-2}$ mol/$g_{cat}$/minute. More preferably, the solution flow rate is preferably from about 2.5 to about 10 ml/minute, and the flow of the alpha ketocarbonyl compound is from about $2 \times 10^{-4} - 3 \times 10^{-3}$ mol/$g_{cat}$/minute.

The modifier flow rate is preferably from about $2 \times 10^{-9}$ to about $2 \times 10^{-4}$ mol/$g_{cat}$/minute, such as, for example, from about $2 \times 10^{-8}$ to about $7 \times 10^{-6}$ mol/$g_{cat}$/minute.

Hydrogen is continuously fed into the fixed bed reactor via flow line (3) containing a compressor (4) and a pressure control system (5). The inert gas, e.g. nitrogen, is fed into the reactor (2) via line (7).

The hydrogen flow rate into the reactor is metered and monitored by a rotameter. Suitable hydrogen flow rates are from about 0.0001 mol/minute (2.4 ml/minute) to about 1 mol/minute (24000 ml/minute), for example, from about $5 \times 10^{-6}$ to about 10 mol/$g_{cat}$/minute.

The hydrogenation reaction can be carried out at a relatively low temperature ranging between about −20° C. and about 100° C., the preferred temperature range is from about −10° C. to about 50° C., such as for example from about 0° C. to about 20° C.

The pressure in the reactor is suitably adjusted to between about 2 bar and about 150 bar, preferably from about 40 bar to about 100 bar.

The effluent from the hydrogenation reaction zone is fed over a two-step expansion module (6) to a separator where the alpha hydroxy carbonyl compound is recovered.

Figure 2:
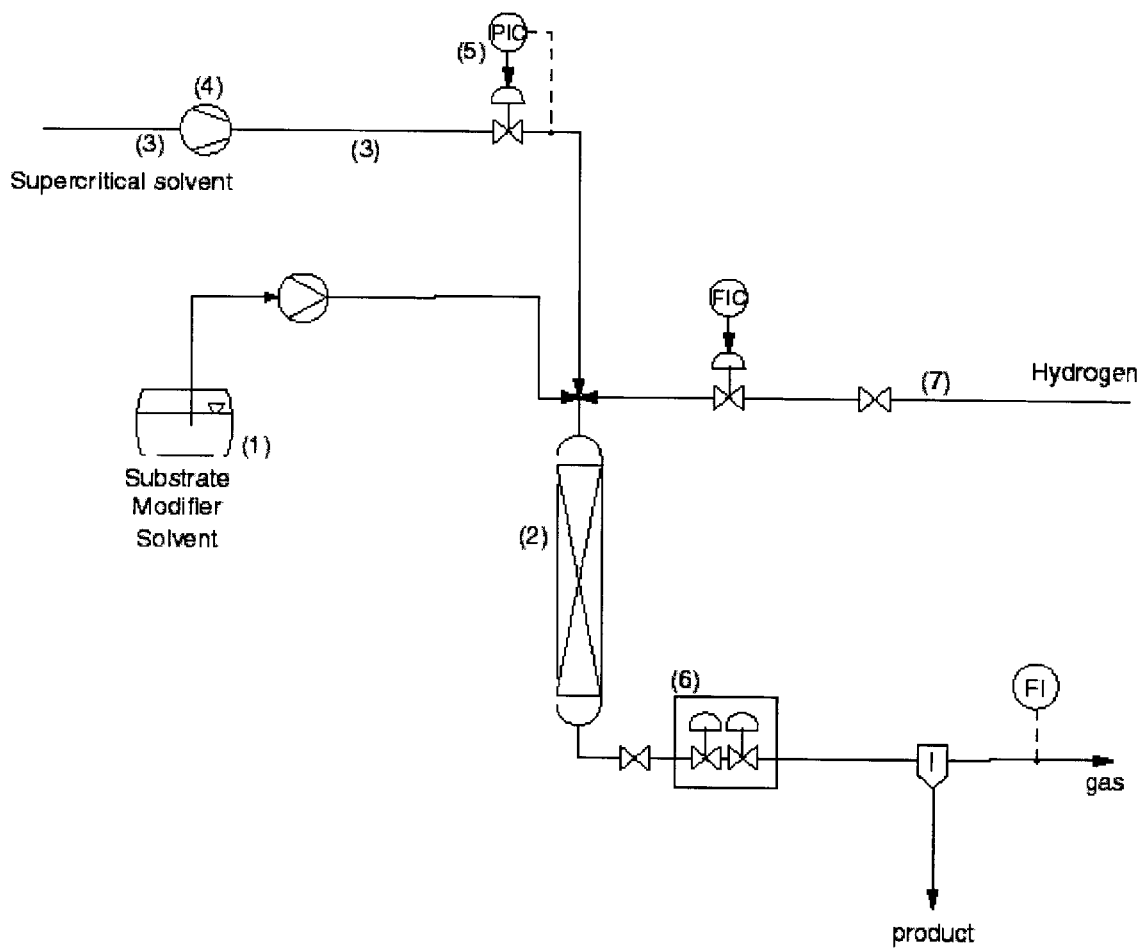
FIG. 2 shows a flow diagram (in schematic form) of a hydrogenation apparatus according to another embodiment of the invention. The reactor vessel is charged with a supercritical solvent. Examples 3 and 4 of the invention refer to a hydrogenation carried out according to FIG. 2.

The process set forth in FIG. 2 is initiated by dissolving the alpha ketocarbonyl compound and the modifier in vessel (1) or by adding a solution containing the modifier to a liquid alpha ketocarbonyl compound. The resulting solution has the following concentration:

about 0.1 wt % to about 100 wt % of alpha ketocarbonyl compound; and about $1 \times 10^{-6}$ wt % to about 0.5 wt % of modifier.

The reactor vessel (2) is charged with a supercritical solvent via flow line (3) containing a compressor (4) and a pressure control system (5).

The organic flow is started at a reaction temperature of, for example, about 50° C. (Example 3) or 36° C. (Example 4). The solution set forth above is pumped into the fixed bed reactor (2) and contacted with hydrogen to start the hydrogenation reaction.

Subsequently, the content of vessel (1) is continuously pumped into the fixed bed reactor with the same solution flow rate as in the process according to FIG. 1.

The flow rate of the supercritical co-solvent is preferably from about 50 ml/minute to about 5000 ml/minute.

When using a liquid alpha ketocarbonyl compound, the supercritical co-solvent is used with a flow rate of about 50 ml/minute to about 5000 ml/minute.

The modifier flow rate is preferably from about $2 \times 10^{-11}$ to about $2 \times 10^{-4}$ mol/$g_{cat}$/min.

Hydrogen is continuously fed into the fixed bed reactor via flow line (7) containing a pressure control system (5). The hydrogen flow rate into the reactor was metered and monitored by a rotameter.

Suitable hydrogen flow rates are from about 0.0001 mol/minute (2.4 ml/minute) to about 1 mol/minute (24000 ml/minute) such as for example from $5 \times 10^{-6}$ to about 10 mol/$g_{cat}$/minute.

The hydrogenation reaction can be carried out at a relatively low temperature ranging between about 20° C. to about 100° C., preferably from about 30° C. to about 60° C., such as for example from about 35° C. to about 50° C. The pressure is suitably adjusted to between about 2 bar to about 150 bar, preferably about 40 bar to about 100 bar.

TABLE 1

Summary of Data From Examples 1–4

| | Example No. | | | |
|---|---|---|---|---|
| | 1 | 2 | 3 | 4 |
| Substrate | Alpha keto-pantolactone | Pyruvic acid ethyl ester | Alpha keto-pantolactone | Pyruvic acid ethyl ester |
| Solvent | Toluene | Toluene | Toluene/Supercritical Ethane | Supercritical Ethane |
| Solvent flow (ml/min) | 5 | 5 | 5/4800 | 750 |
| Substrate flow (mol/min) | $3.9 \cdot 10^{-4}$ | $7.6 \cdot 10^{-4}$ | $3.9 \cdot 10^{-4}$ | $4.3 \cdot 10^{-3}$ |
| Modifier | | Cinchonidine | | |
| Modifier flow (mol/min) | $1.1 \cdot 10^{-6}$ | $5.7 \cdot 10^{-7}$ | $1.1 \cdot 10^{-6}$ | $4.2 \cdot 10^{-6}$ |
| Hydrogen flow (ml/min) | 80 | 80 | 1019 | 927 |
| Temperature (° C.) | 17 | 20 | 50 | 36 |
| Pressure (bar) | 40 | 40 | 100 | 60 |
| Catalyst | | 5 wt % Pt/alumina Engelhard 4759 | | |

TABLE 1-continued

Summary of Data From Examples 1–4

| | Example No. | | | |
|---|---|---|---|---|
| | 1 | 2 | 3 | 4 |
| Catalyst amount (g) | 1 | 1 | 1 | 0.5 |
| Conversion (%) | 100 | 86.4 | 100 | 95 |
| ee (%) | 79.7 | 89.9 | 62.1 | 74.8 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A continuous process for enantioselective hydrogenation of a substrate containing an alpha ketocarbonyl compound comprising the steps of:
   (i) contacting in a reactor charged with a platinum catalyst a substrate solution, a modifier for the platinum catalyst and hydrogen at a temperature of from about −20° C. to about 100° C. and at a pressure from about 2 bar to about 150 bar to convert the alpha ketocarbonyl compound to an alpha hydroxy carbonyl compound;
   (ii) continuously feeding the substrate to the reactor;
   (iii) continuously feeding modifier into the reactor;
   (iv) continuously feeding hydrogen to the reactor;
   (v) continuously discharging a reaction product from the reactor; and
   (vi) recovering the alpha hydroxy carbonyl compound from the reaction product.

2. A process according to claim 1 wherein the substrate is a liquid alpha ketocarbonyl compound or a solution of a solid alpha ketocarbonyl compound.

3. A process according to claim 2 wherein the liquid alpha ketocarbonyl compound is pyruvic acid ethyl ester.

4. A process according to claim 2 wherein the solid alpha ketocarbonyl compound is alpha ketopantolactone.

5. A process according to claim 1 wherein a solid alpha ketocarbonyl compound is dissolved in an organic solvent, a mixture of an organic solvent with water, or a mixture of organic solvents with water.

6. A process according to claim 1 wherein a liquid alpha ketocarbonyl compound is mixed with an organic solvent, a mixture of an organic solvent with water, or a mixture of organic solvents with water.

7. A process according to claim 5 wherein the organic solvent is selected from the group consisting of toluene, benzene, cumene, hexane, cyclohexane, pentane, cyclopentane, diethylether, tetrahydrofuran, acetic acid, ethanol, propanol, acetone, dimethylformamide, and mixtures thereof.

8. A process according to claim 1 wherein the platinum catalyst is a platinum deposited onto a support, which support is selected from the group consisting of carbon black, calcium carbonate, alumina, silica, and zeolithes.

9. A process according to claim 8 wherein the modifier is a solution of cinchona-alkaloid or derivatives thereof, 2-hydroxy-2-aryl-ethylamine or derivatives thereof, or 1-aryl-ethylamine or derivatives thereof.

10. A process according to claim 8 wherein the platinum catalyst contains about 0.5 wt % to about 10 wt % of platinum deposited onto alumina.

11. A process according to claim 10 wherein the modifier is a solution of cinchonidine or dihydrocinchonidine.

12. A process according to claim 1 wherein the substrate solution contains from about 0.1 wt % to about 100 wt % of an alpha ketocarbonyl compound and from about $1 \times 10^{-6}$ wt % to about 0.5 wt % of a modifier.

13. A process according to claim 1 wherein the hydrogenation reaction is carried out at a temperature from about −10° C. to about 50° C. and at a pressure from about 40 bar to about 100 bar.

14. A process according to claim 1 wherein the hydrogenation reaction is carried out at a temperature from about 0° C. to about 20° C.

* * * * *